US012766105B2

(12) United States Patent
Allen et al.

(10) Patent No.: US 12,766,105 B2
(45) Date of Patent: Oct. 20, 2026

(54) MEDICAL TREATMENT DELIVERY SYSTEM EMPLOYING SUBCUTANEOUS IMPLANTS FOR SUSTAINED MEDICATION RELEASE

(71) Applicants: David Lee Allen, Union, OH (US); Josette Marie Allen, Union, OH (US); Peter McDuffie White, Bonham, TX (US)

(72) Inventors: David Lee Allen, Union, OH (US); Josette Marie Allen, Union, OH (US); Peter McDuffie White, Bonham, TX (US)

(73) Assignee: Buffalo Pacific, LLC, Troy, OH (US)

( * ) Notice: Subject to any disclaimer, the term of this patent is extended or adjusted under 35 U.S.C. 154(b) by 431 days.

(21) Appl. No.: 18/461,313

(22) Filed: Sep. 5, 2023

(65) Prior Publication Data

US 2024/0016740 A1 Jan. 18, 2024

Related U.S. Application Data

(62) Division of application No. 17/003,251, filed on Aug. 26, 2020, now abandoned.

(51) Int. Cl.
*A61K 9/16* (2006.01)
*A61K 9/00* (2006.01)
(Continued)

(52) U.S. Cl.
CPC .............. *A61K 9/16* (2013.01); *A61K 9/0024* (2013.01); *A61K 31/485* (2013.01); *G16H 10/65* (2018.01);
(Continued)

(58) Field of Classification Search
CPC ...... A61K 9/16; A61K 9/0024; A61K 31/485; A61K 47/12; G16H 10/65; G16H 20/70; G16H 30/00; G16H 40/67; G16H 20/17
See application file for complete search history.

(56) References Cited

U.S. PATENT DOCUMENTS 6,582,441 B1 * 6/2003 He .................... A61N 1/0551 604/59
6,964,370 B1 * 11/2005 Hagale ................ A47C 31/008 297/217.3
(Continued)

FOREIGN PATENT DOCUMENTS

WO WO-9830171 A1 * 7/1998 ........... A61K 9/0024

OTHER PUBLICATIONS

Lobmaier et al [CNS Neurosci., pp. 629-636] Naltrexone Depot Formulations (Year: 2011).*

*Primary Examiner* — John A Tweel, Jr.
(74) *Attorney, Agent, or Firm* — R. William Graham

(57) ABSTRACT

A comprehensive addiction treatment method with a medication delivery system of subcutaneous implant of micropellets in patients, which may include a method of identification at an advanced video communication system through facial recognition, voice recognition and/or a recognition of an RFID microchip implanted in a patient. The identification will be transmitted over the Internet to a database at a secure server to initiate a computer program to stream video content, computer generated communication and/or a live video to be transmitted to an audio-visual system that may be capable of displaying a life-size video image of a live caregiver or a computer generated avatar of a caregiver within a three dimensional setting for real time two-way communication with apparent eye contact.

20 Claims, 8 Drawing Sheets

(51) Int. Cl.

| | |
|---|---|
| ***A61K 31/485*** | (2006.01) |
| ***G16H 10/65*** | (2018.01) |
| ***G16H 20/70*** | (2018.01) |
| ***G16H 30/00*** | (2018.01) |
| ***G16H 40/67*** | (2018.01) |

(52) U.S. Cl.

CPC ............. *G16H 20/70* (2018.01); *G16H 30/00* (2018.01); *G16H 40/67* (2018.01)

(56) References Cited

U.S. PATENT DOCUMENTS

| | | | | |
|---|---|---|---|---|
| 7,473,431 | B2 * | 1/2009 | Tice ..................... | A61K 31/485<br>424/424 |
| 12,412,440 | B2 * | 9/2025 | Joao ....................... | G07C 13/00 |
| 2005/0062844 | A1 * | 3/2005 | Ferren ...................... | H04N 7/15<br>348/E7.083 |
| 2006/0212096 | A1 * | 9/2006 | Stevenson .............. | A61B 90/90<br>607/60 |
| 2011/0307284 | A1 * | 12/2011 | Thompson ............. | G16H 10/60<br>705/7.13 |
| 2013/0066647 | A1 * | 3/2013 | Andrie ................... | G16H 20/40<br>705/2 |
| 2015/0138303 | A1 * | 5/2015 | White .................... | H04N 7/144<br>348/14.07 |

* cited by examiner

MEDICAL TREATMENT DELIVERY SYSTEM EMPLOYING SUBCUTANEOUS IMPLANTS FOR SUSTAINED MEDICATION RELEASE

TECHNICAL FIELD

This present invention relates to treatment systems and methods addressing multiple aspects to provide a comprehensive recovery program for addictions, chronic conditions and diseases.

BACKGROUND

It is well known that drug and alcohol addiction have negative consequences in people's lives and affects the productivity of our society. Furthermore, there are autoimmune diseases, such as Grave's disease, lupus, and multiple sclerosis, that require extensive care programs. There are many treatment systems and methods available, however there is a need for a comprehensive program that improves effectiveness and results in saving lives, reducing suffering in the ones addicted, the family and the extended community.

The Substance Abuse and Mental Health Services Administration, the US Surgeon General, the National Institute on Drug Abuse, and the Centers for Disease Control and Prevention have a substantial body of research evidence supporting treatment with buprenorphine or methadone, which have been demonstrated to be highly effective in managing the core symptoms of opioid use disorder, reducing the risk of relapse and fatal overdose, and encouraging long-term recovery. However, buprenorphine or methadone are substitutes for illicit drugs and may not overcome the root causes of addiction or chronic condition.

Alternatively, Naltrexone belongs to a class of drugs known as opiate antagonists, which works in the brain to prevent opiate effects (e.g., feelings of well-being, pain relief). It also decreases the desire to take opiates. This medication is also used to treat alcohol abuse and chronic conditions.

The typical treatment method for buprenorphine, methadone and Naltrexone is prescribed pills to be taken daily. This method has poor results with compliance since the addicts may not take the pills every day in an attempt to avoid the cost of further prescriptions, or they simply forget to take the medication each day as prescribed.

Another problem is that addicts may take excessive amounts of pills at one time. This problem may be addressed by requiring the addict to go to a dispensary each day to receive the prescribed amount of medication. This presents a challenge for addicts to get transportation to the clinic every day.

Another problem is that addicts may receive the pills through a recovery program but sell them to other addicts to receive money for the purchase of heroin or other illicit drugs. In some cases, they may deliberately avoid taking the opiate antagonists, which prevent opiate effects, in order to get the high that they crave from illicit drugs.

The problems associated with treatments based on delivery of medication in pill form have been addressed by an extended-release injectable suspension. By way of example, one commercially available treatment method is Vivitrol, which is based on a Naltrexone formulation for deep injection containing 380 mg of the medication per vial. The extended-release injections of Vivitrol provide treatment for 21 to 30 days.

However, these injections may cause severe reactions at the site of injection. Some people on Vivitrol have had severe injection site reactions, including tissue death. Some of these reactions have required surgery. This Vivitrol method incurs a major financial commitment in that the Vivitrol injections may cost $1,600 or more per month compared to the wholesale cost of Naltrexone in pill form that may be approximately $24 per month.

Another more recently developed system is the delivery of Naltrexone in medication pellets that get inserted under the skin for slowly releasing the medication over varying lengths of time—usually from 2 to 6 months. In one system of subcutaneous implantation a 1" long pellet is surgically implanted in an incision requiring stitches. The implant is typically placed under the skin in the area of the abdomen where it has the undesirable result of a visible bulge with stitches. The implementations to date are primarily experimental and investigational.

For motivated users who are committed to abstinence, the Naltrexone implant may lower the risk of a relapse by reducing the craving for opioids. In combination with therapy and behavioral modification, Naltrexone can help reduce the desire for drugs. While it is a helpful treatment tool, Naltrexone doesn't "cure" opiate addiction, and the drug won't be effective unless the Client is motivated to recover.

In addition to the need for a comprehensive recovery program for addictions, there is a need for an improved treatment program for autoimmune diseases. These conditions require the delivery of medication to the patient in a controlled manner over an extended period of time. Over time, various published articles have begun suggesting that a Naltrexone regiment might prove to be helpful to some clients who exhibit autoimmune diseases.

There is a need for a more cost-effective system for administering medication for addiction and non-addiction treatment. Furthermore, there is a need for a more comprehensive program that addresses the need for counseling throughout the recovery process. Hence, there is a need for an improved system that addresses the shortcomings of the prior art mentioned above.

Prior Art Configurations

Previous systems and methods have been used for addiction recovery treatment.

In FIG. 1 the primary method for treatment addiction is with the prescription of medication in a pill form. In the field of addiction treatment, a person participating in a recovery program may be called a Client. In this method the Client 1 initially has a line of communication 5 with an authorized clinic or hospital to undergo an exam 2. As a requirement for medical treatment, the Client 1 must establish a line of communication 8 with a financial method of payment 4, which may be an insurance company, government agency or private payment arrangement. This financial payment method 4 must have a line of communication 9 to the provider of the exam 2.

(1) Upon completing the exam 2 a line of communication 6 is made with a pharmacy or provider of medication 3 to place an order for pills. The pharmacy must make the line of communication 10 with the financial arrangement 4 for purchase of the pills. The Client 1 must have a line of communication 7 for the delivery of the pills or physically travel to the provider 3 of the pills.

The primary problem with this method of treatment is the results in compliance of the Client taking the pills as prescribed. The Client 1 may not remember to take the prescribed pills as needed. Also, the Client 1 may sell the drugs to generate money for the purchase of illicit drugs. Furthermore, there is not an effective method for confirming the identity of the Client 1 as they may not have a permanent address or may not have a driver's license or other identification documentation. This lack of confirmation of identity leaves financial transactions open for fraud, which has been a problem with government funded programs.

In FIG. 2 the Client 1 established a line of communication 5 for an exam 2 at an authorized medical institution. The Client 1 contacts 8 a financial entity 4 for payment 9 for the exam 2. In this method the exam 2 communicates 12 with a provider for an injection 11. The Client 1 travels 13 to the provider for the injection 11 and communicates 14 a method of payment 4.

In this method the Client 1 must return every month for another injection 11. This method overcomes the problems of treatment with pills since the Client 1 has a confirmed treatment for a month. However, there are documented negative side effects from the injection 11. Furthermore, the cost of injections is substantially more expensive than treatment with pills.

In FIG. 3 the Client 1 has a line of communication 5 with a provider for an exam 2. A communication 16 is sent to schedule an implant 15. The Client 1 travels 17 to the medical facility for the implant 15. The Exam facility 2 communicates 9 for the exam payment at the financial entity 4. The financial entity 4 communicates 18 for the payment for the implant 15.

The implant may be a pellet with drugs known as opiate antagonists. The injections may diminish craving for opiates or alcohol. This injection may be Naltrexone or other drugs to address addiction or other medical problems. However, it is well documented that the administration of drugs is only one part of a recovery program.

In FIG. 4 a more complete treatment program is shown. In this example, the method of administering an implant 15 is described. The addition of treatment 20 is added along a line of communication 22 and a payment method 23. This treatment 20 may involve a number of medical evaluations and processes to maintain the health of the Client 1 during the recovery period that may be twelve months or more. Furthermore, in this more comprehensive program counseling 21 is established along a line of communication 25 with payment 24 with the financial 4 arrangement. The need for ongoing treatment 20 and counseling 21 is well documented. However, a comprehensive program is not commonly achieved due to the challenges of establishing relationships with all of the different professional services and the complexity of funding the services.

SUMMARY OF THE INVENTION

It is an object to improve treatment for individuals addictions, chronic conditions and diseases.

It is a further object to provide a medical treatment delivery system using a subcutaneous implant of micro-pellets with medicine for release over time.

A further object is to provide a medical treatment by implanting in a medical delivery system along Langer lines in the horizontal plane surrounding the upper hips and lower back.

Another object is to provide a treatment to aid in combatting opiate addiction.

Still another object is to utilize a medicine, such as Naltrexone combined with stearic acid, to treat addictions, chronic conditions and diseases.

Yet another object is to provide medical treatment delivery system using micro-pellets to release the medicine over a period, such as several months.

A further object is to track the medicine by employing a tracking device therewith.

Still another object is to read the tracking device when positioned at an access point to a video conference system that has an internet connection to the database with the Client's medical records and treatment plan documentation.

A further object is to provide a video conference system which incorporates a two-way mirror between the Client and an image display device positioned for providing the Client with a direct view looking forward at eye level through the two-way mirror at a displayed image on the image display while the two-way mirror is angled at approximately 45 degree to reflect an illuminated panel that is positioned further from the two-way mirror than the image display device and a caregiver at a distant location from the Client is captured by a camera with a display system that achieves a line of sight directly toward the camera and the video image and audio is transmitted over an Internet connection to the location of the Client for appearing on the image display with a perceived eye contact.

A further object is to provide a live computer generated image of an avatar through the system to appear on the image display device for viewing by the Client.

Yet another object is to employ facial recognition that identifies facial expressions to determine the mental state of the Client.

Another object is to identify the Client using facial recognition.

Still other objects employ recording mechanisms regarding the treatment.

The problems and needs outlined above are addressed by preferred embodiments of this present invention. For the purposes of providing a definition of the overall scope and comprehensive aspects of this present invention, it has been coined by the inventors as the "Delaney Method" in honor of Pastor Greg Delaney who has dedicated his life befriending the friendless . . . those in desperate need of recovery. Unlike other systems and methods that only address medical and physical concerns, the Delaney Method addresses the whole person in their need for psychological and emotional support. This specification will describe how the Delaney Method may provide an innovative way to connect Clients with a network of medical professionals, psychologists, and dedicated, compassionate people who care about the well-being of their Clients' lives.

It is well known that treatment of addiction is a challenge for individuals to overcome. It requires the individual to have the emotional commitment for changing their priorities to support the recovery program. In particular, the Clients may have been badly damaged by life's circumstances having become addicted to drugs and/or alcohol. They may succumb to such a low state of health they can barely muster a call for help or possibly can't envision help. These ones may be stripped of life itself, have no reserves and have no reasons to try living again. It is the aspiration of this present invention to provide a method for intersecting with and advocating for these helpless persons. Addiction affects people in their lives to the core of their existence.

The journey in recovery may require finding a new meaning of life. The transformation may involve a religious experience to find a way forward beyond the abyss of addiction. For some people, the teachings of Christianity may provide the guidance. However, no matter what religion or beliefs may provide the foundation for their lives, addicts need to reach into their souls to commit to recovery.

The Delaney Method acknowledges this personal challenge and provides the process and capability to achieve successful recovery. This method utilizes an innovative communications technology to connect Clients with supportive professionals who provide compassion and understanding. Instead of the traditional recovery treatment methods that require Clients to interact with staff at hospitals and clinics, the Delaney Method provides face-to-face counseling and supportive consultation through live video communication. Whereas typical video communication is a display of a person on a flat screen appearing from a remote location, the Delaney Method is delivered with a patented communications technology, called Holographical Reality, where a transmitted person appears life-size three dimensionally in front of the Client with eye contact for a natural human interaction. The Client does not need to wear 3D glasses or a virtual reality headset.

The advantage of Holographical Reality compared to video conferencing is that the sense of presence and personal connection with eye contact establishes a feeling of trust in the honest compassion and belief in caring that is essential for reaching into the depth of the emotional soul of the Client as they struggle with the challenges of overcoming addiction.

The practical advantage of Holographical Reality is that the professionals delivering the treatment of the Delaney Method can reach out to their Clients over a distance. This overcomes the widespread problem of limited availability of Doctors, clinicians and psychiatrists with the training to provide treatment for addicts. In particular, the Clients may live in areas where there are no such professionals in close proximity.

For the purposes of description for this present invention Holographical Reality communication will be delivered in a suite of furniture and equipment, called the "Omni-Carriage". The Omni-Carriage will provide a chair for the Client and table between the Client and the teleported professional caregiver appearing life-size three dimensionally across the table from the Client while making eye contact during two-way communication in real time.

This Omni-Carriage will be networked to the servers of the national or international database, called an "Omni-Server".

In the Delaney Method a Client may go to a physical location of a building or suite of offices, called an "Omni-Portal", that is equipped with one or more Omni-Carriages with a network connection to the Omni-Server to manage the advanced video communication, A new Client will be greeted by a staff member or an Omni-Avatar for an introduction to the treatment program. An Omni-Avatar is video or a computer generated lifelike image of a staff member that is displayed as a life-size, three dimensional image on a Holographical Reality system. The Omni-Avatar will respond to sensors that may include motion sensors, proximity sensors, video recognition, voice recognition, and/or other methods of recognizing a person's presence and interaction. The sensors will trigger responses from the Omni-Avatar, which may be a preprogrammed series of video segments based on responses by the Client or may be based on the logic of an Artificial Intelligence program to generate live computer generated responses by the Omni-Avatar. A staff member or the Omni-Avatar will take the basic information for enrollment, however, professionally qualified Doctors and psychiatrists will conduct the Client evaluation over a distance using Holographical Reality.

In accordance with one embodiment of the present invention, the method of administering a pellet with a medication is further refined with a system based on "micro-pellets". This system is an innovative step in that it overcomes the problems associated with the present embodiment of pellets with medication and their insertion.

The micro-pellets, which are smaller than a grain of rice, do not require a surgical incision with the resulting need for stitches. The micro-pellets are injected beneath the skin without the need for surgery. The site of the injection recovers within one or two days and does not leave a scar. With the administration of a local numbing agent, the Client will not feel pain during the ten minute procedure.

A first implementation may include four micro-pellets that may be 250 mg each. These may be spaced a quarter of an inch or more apart. With this system of proprietary micro-pellets, the Client may receive a slow release of the medication over a duration of 90 days. The comprehensive program of this present invention may have a one year protocol. Following 90 days a second insertion may include 3 micro-pellets for 750 mg of medication. This may be followed with a third insertion of 2 micro-pellets for 500 mg and a fourth insertion of 1 micro-pellet for 250 mg.

In the system of the present invention the insertion may be positioned along "Langer Lines". These Langer Lines are defined by the integral grain of the skin, which is aligned to allow for stretching in the direction of movement surrounding the body. In this embodiment the selected Langer Lines may be along the horizontal alignment surrounding the hip along the beltline, namely, between and parallel with the Langer Lines. The specific location of insertion may be along this horizontal Langer Line at the back portion of the body. In order to minimize the sensation of awareness of the insertion within individuals, a right handed person may have the insertion in the left portion of the back. Conversely, a left handed person may have the insertion in the right portion of the back.

The micro-pellets may be a proprietary formulation of medication for the addictive or non-addictive treatment. For drug addiction the medication may include stearic acid that will support the effective medical delivery of the opiate antagonist medication over a 90 day period. For autoimmune diseases the medication may be specific to the disease.

An essential aspect of the method of the present invention is the identification of the Client. In particular, the system of implanting micro-pellets provides effective delivery of medication over an extended period of time, but the implant is only one part of the comprehensive treatment program. The present method includes a program of medical treatments and counseling by accredited therapists. This requires that the Client has a method for identification with access to the medical records for the treatment program.

Upon admission to a treatment program, a Client may receive an identification card with a method of reading the Client identity, such as a magnetic strip, ID chip, QR code or other technology for retrieving information. This card may be used upon the return of the Client to a medical treatment location. However, it would be advantageous to have an additional method of identification since the Client may lose the card or forget to bring it to an appointment.

At an initial medical exam, the Client may be able to prove his or her identity. However, during a treatment period that may have a duration of twelve months, they may not retain the identity card. In the case of an incident needing medical attention, the Client could suffer serious consequences or even death if there is not a way to quickly confirm the contents of their imbedded medication.

Clients with alcohol or drug addiction may not have standard forms of identification, such as a driver's license. They may not have a permanent address. It may be that these Clients do not have medical insurance cards since they may not have any form of insurance. While they may remember their social security number, the confirmation of their identity may be difficult considering their addictive condition. The Client could be given identifying codes or passwords, but these may be forgotten. They may start their treatment at one clinic but over the duration of the treatment program they may move to another city or another state.

Therefore, it is important to be able to prove the identity of the Client through the duration of the treatment program. The preferred method of identification is to avoid a manual process of reviewing paperwork or manually logging into various databases to access information that can be both time consuming and unreliable. It is thus another objective of this present invention to implement identification methods that are both instantaneous and automated to initiate video communication programs and live video communications that are specific to the Client at the appropriate stage of their treatment program. This Delaney Method may quickly and efficiently identify the Client to receive the treatment services of their program without needing to fill out any paperwork upon arriving at any Omni-Portal.

In another embodiment of the present invention the Omni-Carriage will facilitate one or more methods for identification.

A camera, as an integral component of the Omni-Carriage, will capture an image of the Client seated in a position for a counseling session. A high definition digital photo and/or a video segment may be captured to be stored within the database of the Omni-Server where it will be saved in the medical records of the Client. Upon the initiation of a counseling session, the digital photo or video may be used to identify the Client. In a further method of identification, a microphone as an integral component of the Omni-Carriage may capture an audio recording of the Client to be stored at the database of the Omni-Server for identification by voice recognition.

Additionally, a facial recognition system may be integrated into the Omni-Carriage for the purpose of providing an accurate identity of the Client. In a further method of identification, a significant and yet non-obvious embodiment of this present invention is the insertion of a Radio Frequency Identification Device at the time of the first insertion of the micro-pellets. In this system the selected RFID microchip may be smaller than a grain of rice. It would be inserted in a similar method as the micro-pellets and would be inserted at the same time as the procedure for the micro-pellets with medication. This would not require any significant additional time for the procedure and would not impose an additional inconvenience upon the Client.

An Omni-Carriage may incorporate an interrogator scanning device to instantly read the code within the microchip, which may be linked to a computer within the Omni-Carriage that is networked to the Omni-Portal for identification of the Client. The interrogator may be integrated in the back of the chair within the Omni-Carriage to be positioned within 10 cm (4") of the placement of the microchip in the back of the Client.

In this embodiment the RFID microchip would be passive in that it would not have a battery or any internal power source. In this regard, it would be completely inert. The microchip would never wear down and could be good for the lifetime of the Client. The specified RFID may be glass encapsulated so that it is biocompatible. This means that it would be non-toxic and would not have any allergic reaction or other adverse effect on the human body.

The microchip may include a cap made of polypropylene polymer to keep the chip from moving around once it is inserted. The polymer works by encouraging connective tissue and other kinds of cells to form around the capsule to hold it in place.

Inside the capsule is a silicon microchip, a tuning capacitor and an antenna coil. In order to retrieve the information on the microchip an interrogator performs the function of energizing the antenna coil to activate the capacitor to read the microchip. When set at the specified frequency the interrogator scans the microchip to receive an identification number.

It is important to note that the microchip only provides an identification number, which does not reveal any personal information about the Client. This ID number is only meaningful when used as identification within an external database. In this regard the application of an RFID microchip meets all HIPAA privacy requirements for confidential medical information or any other privacy requirements. Furthermore, the microchip can be simply removed by a small incision at any time during the treatment or following the completion of the treatment program.

The comprehensive treatment system of this present invention based on an implanted microchip establishes a platform for the delivery of an extensive host of innovations in the care for Clients needing addiction recovery treatment that has not been possible with previous systems. The simple ID number establishes a link to a database accessed over the Internet for the full scope of innovative services.

While it is important to confirm identity, it is essential that the Client's medical records are confidential. Clients may not want information about an addiction recovery program on their personal record. For these reasons it would be undesirable for the identity of the Client to be recorded by permanent physical methods, such as fingerprints, iris scans or tattoos.

The identification method of this present method using a microchip solves the problems presented above. The microchip does not contain any confidential information since it only retains a single identification number. Furthermore, the microchip is not physically visible when inserted and can be removed at any time during or after the treatment program.

One of the unique benefits of the method using a microchip is that a Client could undergo a treatment program without ever revealing any of their personal information. This may be of extreme importance for individuals who need addiction recovery treatment, but do not want their condition to be known to their employers, insurance providers or other people. These anonymous individuals could undergo their exam for confirmation of their medical condition and pay for their treatment in cash. They could receive the insertion of the micro-pellets and microchip for the treatment. For the duration of the program they would only need to provide access to the code on their microchip to continue with all aspects of treatment.

Another aspect of the present invention is that the method of using visual recognition, voice recognition or a microchip for identification would eliminate the liability of fraud during treatment. The Client could not sell the treatment services to another individual or claim treatment that was not delivered since their identity is confirmed. It may be of particular value to government funded programs where confirmation of services can be validated for recipients.

Further advantages of the above described methods of identity verification may be evident during the treatment period. As the Clients proceed with the program of medical procedures and counseling, the identity will need to be verified multiple times. If the Client is in a poor cognitive state during drug or alcohol recovery their ability to communicate effectively may be compromised. Also, the Client may be of a different nationality and may not have command of the English language to establish their identity.

Once the client is identified at an Omni-Carriage, the Omni-Server database is triggered to initiate the current program for the Client. This may be a pre-programmed video content that will appear in the Omni-Carriage as a Holographical Reality display. This content may be a video image of a person welcoming the Client upon their return for treatment. The selection of the video content may be determined by a sophisticated Artificial Intelligence (AI) program that will present a communication response that is uniquely appropriate for the Client. The AI response may be a selected pre-recorded video of a caregiver welcoming the Client back. Alternatively, the video may be a real time, computer generated avatar appearing life-size in a highly realistic human embodiment. In this modality, the same avatar that previously greeted and met with the Client will reappear essentially providing comfort (through continuity) that the same doctor is bedside or in the room with the Client.

The Omni-Carriage includes a high definition camera to capture a video image that is transmitted to be viewed by the caregiver for live two-way communication. This same video image may be analyzed by a computer for AI evaluation of facial recognition that may provide information about the emotional state of the Client. The combination of the information in the medical records within the Omni-Server on the Client and their AI evaluation of their condition will determine the assignment of the appropriate caregiver to be teleported to the Omni-Carriage.

It is the strategy of the present invention to develop a network of thousands of Omni-Portals equipped with Omni-Carriages for Clients to access within a reasonable driving distance. The caregivers will be logged into the Omni-Server over a network to be available for transmission to Omni-Carriages. In cases where the Clients have scheduled follow-up meetings, the Client will go to the nearest Omni-Portal for the scheduled session with the assigned caregiver for their treatment. There would not be a need to return to the location at the beginning of the treatment, since each Omni-Carriage at any location in the country would access the same Omni-Server database and resource of caregivers for live video communication. In this way services can be delivered without the limitations of geographic proximity. If there is a need for the Client to make contact to a caregiver for an unscheduled time, the next available caregiver will be teleported to the Omni-Carriage for meeting with the Client.

The network of locations may expand as the organization has the resources to install thousands of Omni-Carriages throughout the United States in counties, cities, towns and townships. One preferred method for this expansion is to incorporate an Omni-Carriage within a self-contained module. The term "module" can be related to the association with the "lunar module" used for the enclosure for the astronauts during the trip to the moon. In this context, an "Omni-Module" could be the enclosure for an Omni-Carriage where a Client would be teleported to another part of the country or another part of the world. An Omni-Module may be no larger than the size needed for an Omni-Carriage system with seating to accommodate a Client for a Holographical Reality experience with a caregiver being teleported from another location. The size of the footprint of the Omni-Module may be approximately 5' wide and 7' long.

The Omni-Module may not have windows or openings that would allow visual access from the outside. Furthermore, the Omni-Module may contain the audio of the communication within the enclosure by the means of construction and acoustic treatment so that the voices of the participants cannot be heard outside. In order to further assure that the voices of the participants are not recognizable from outside of the room a generator of white noise may be used to mask the voices.

An Omni-Module will be small enough that it could be set in available spaces in community centers, churches, local government facilities, etc. Furthermore, it could be licensed to be installed within commercial venues, such as Walmart, CVS, Walgreens, etc. With a national network in the United States, Clients could go to any Omni-Module to have their caregiver teleported to meet with them.

An Omni-Module would have an identification method to authorize entry by a Client without any staff at that location. The identification may be by an issued ID card, facial recognition, voice recognition, RFID chip or other approved identity method. With approval of identity of a Client the door to the Omni-Module would be unlocked and the Omni-Server database would be instantly retrieved for the Client. Upon entering the Omni-Module the Holographical Reality visual and audio content would be initiated. One of the advantages of Omni-Modules is that the Clients could gain access to addiction services even in locations where there are not medical staff present or caregivers within hundreds of miles. A further advantage of Omni-Modules is that Clients could seek help without revealing to people in their community that they have addiction problems. In traditional methods of treatment the addicts need to meet with staff members of the treatment facilities in their own community for care. As a result, many addicts may not seek treatment due to their fear of being recognized during treatment and risk being outcast within their community.

A rollout of thousands of Omni-Portals and Omni-Modules could be through franchises to healthcare corporations, national pharmacies, stores, investors, etc.

The Delaney Method has the potential of helping people worldwide with the ability to deliver care remotely.

The Delaney Method may be licensed to governments or healthcare services of other countries and franchisees in any country. The principles of the Omni-Portal, Omni-Carriage, Omni-Server and Omni-Module may remain the same on a global scale. However, the implementation in each country may be managed in the language of the country and operated within the regulations for insurance and legal requirements of their government managed through a Global Server.

BRIEF DESCRIPTION OF THE DRAWINGS

The above features of the present invention will be more clearly understood from consideration of the following descriptions in connection with accompanying drawings in which.

DETAILED DESCRIPTION OF ILLUSTRATIVE EMBODIMENTS

Figure 1:
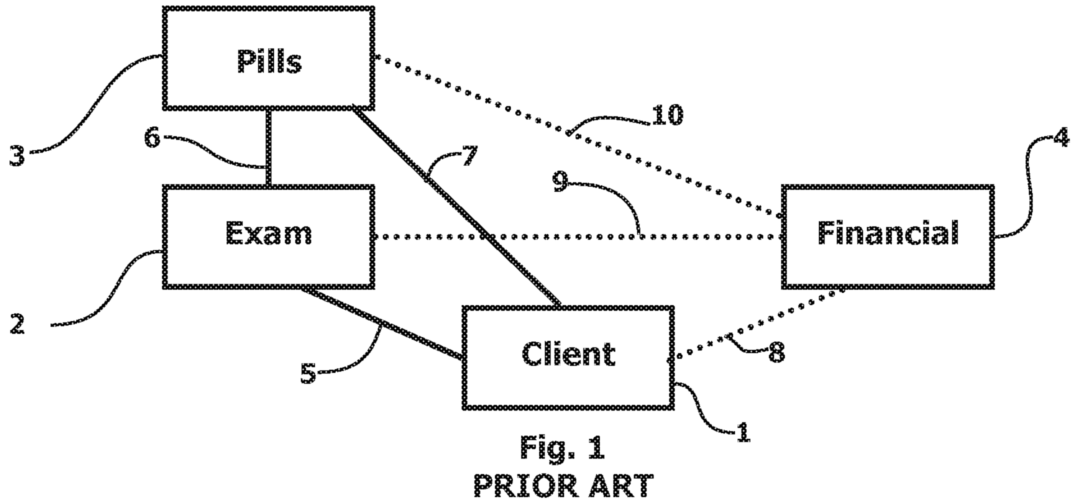
Fig. 1 PRIOR ART
FIG. 1 illustrates a prior art configuration of treatment based on medication in a pil format.
Figure 2:
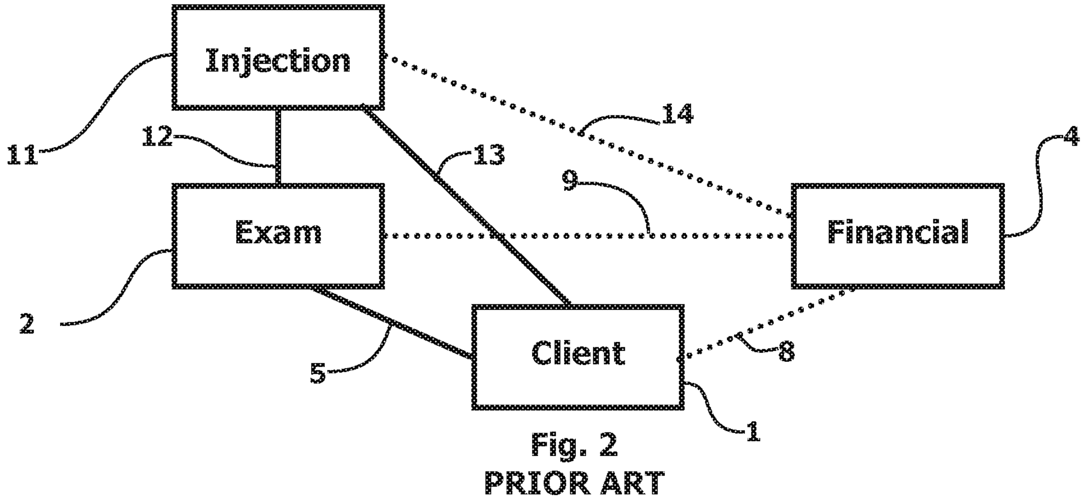
Fig. 2 PRIOR ART
FIG. 2 illustrates a prior art configuration of treatment based on medication administered ni an injection.
Figure 3:
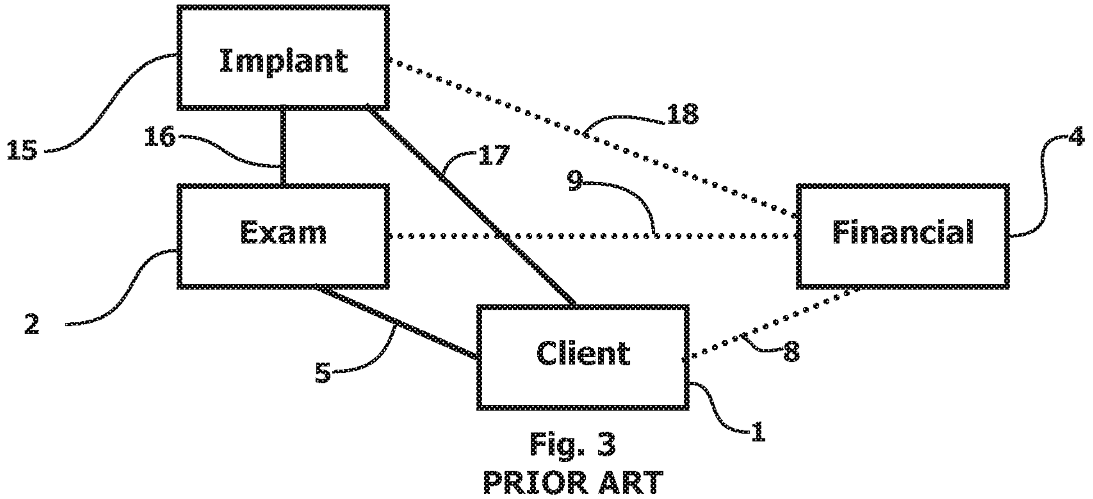
Fig. 3 PRIOR ART
FIG. 3 illustrates a prior art configuration of treatment based on a subcutaneous implantation of a pellet comprised of medication.
Figure 4:
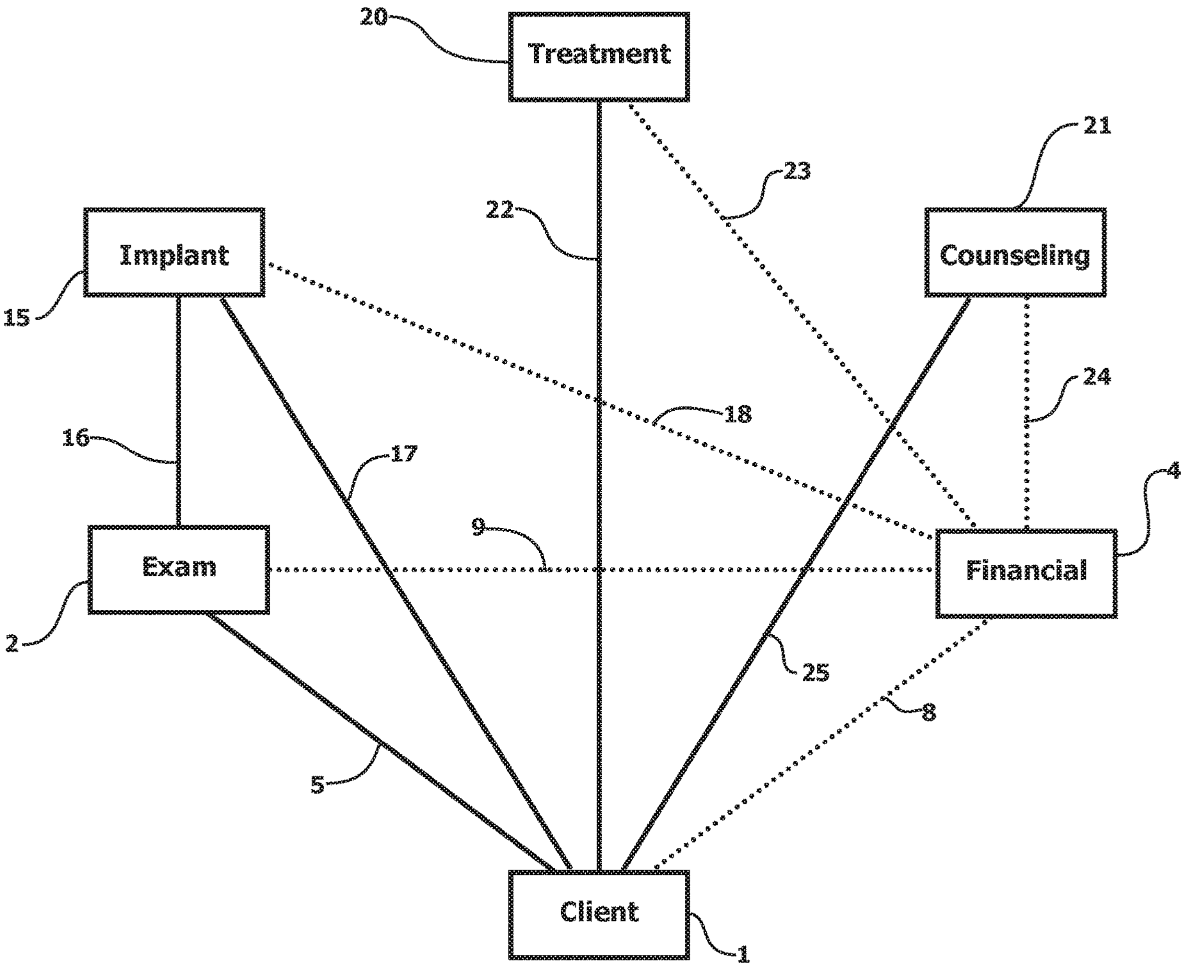
Fig. 4 PRIOR ART
FIG. 4 illustrates a prior art configuration of a comprehensive program including medical treatment and counseling during the recovery period.

Referring now to the drawings, wherein like reference numbers are used to designate like elements throughout the various views, several embodiments are further described. One of ordinary skill in the art will appreciate the many possible applications based on the following examples of possible embodiments.

As a prelude to the method of implementing the invention, the following practice procedure can be employed.

A potential Client is identified and the Client is interviewed by medical intake personnel. Upon determining the Client wants to access help and proceed with treatment, the Client is interviewed by Disease Manager (DM) specialist via a facility.

DM Psychiatrist and Team DM determine that Client is a viable candidate taking into account predetermined condition factors.

Psychiatrist writes prescription for a predetermined period, e.g., 1 year protocol. The prescription includes prescribing 10 DM micro pellets, wherein DM micro pellets contain 250 mg Naltrexone.

The prescription is followed and continually monitored at the facility and adjusted from time to time as needed, for the first 3 months, then 3 more months, then 3 more months, then final 3 months.

Administration of the prescription.

Patient lies face down on an exam table, skin on the back of the client is cleansed and local anesthesia is applied.

Surgeon cuts ¼ inch long, subcutaneous dashes into selected langer lines with ½ inch between the dashes.

DM micro pellets are inserted.

Openings are sealed with steri strips (no stitches needed).

Left to right if patient is right handed; right to left if patient is left handed.

Patient commences receipt of hydration therapy according to written prescription.

Patient is assigned to daily IOP (individual and group).

IOP therapy begins same day.

Once the initial procedure is complete, a new life begins including all normal lifestyle activities and is monitored for 1 year. A graduation ceremony is provided as part of a mental achievement and the patient enters the "Service of others Program" as a lifestyle for reinforcement of their treatment.

Figure 5:
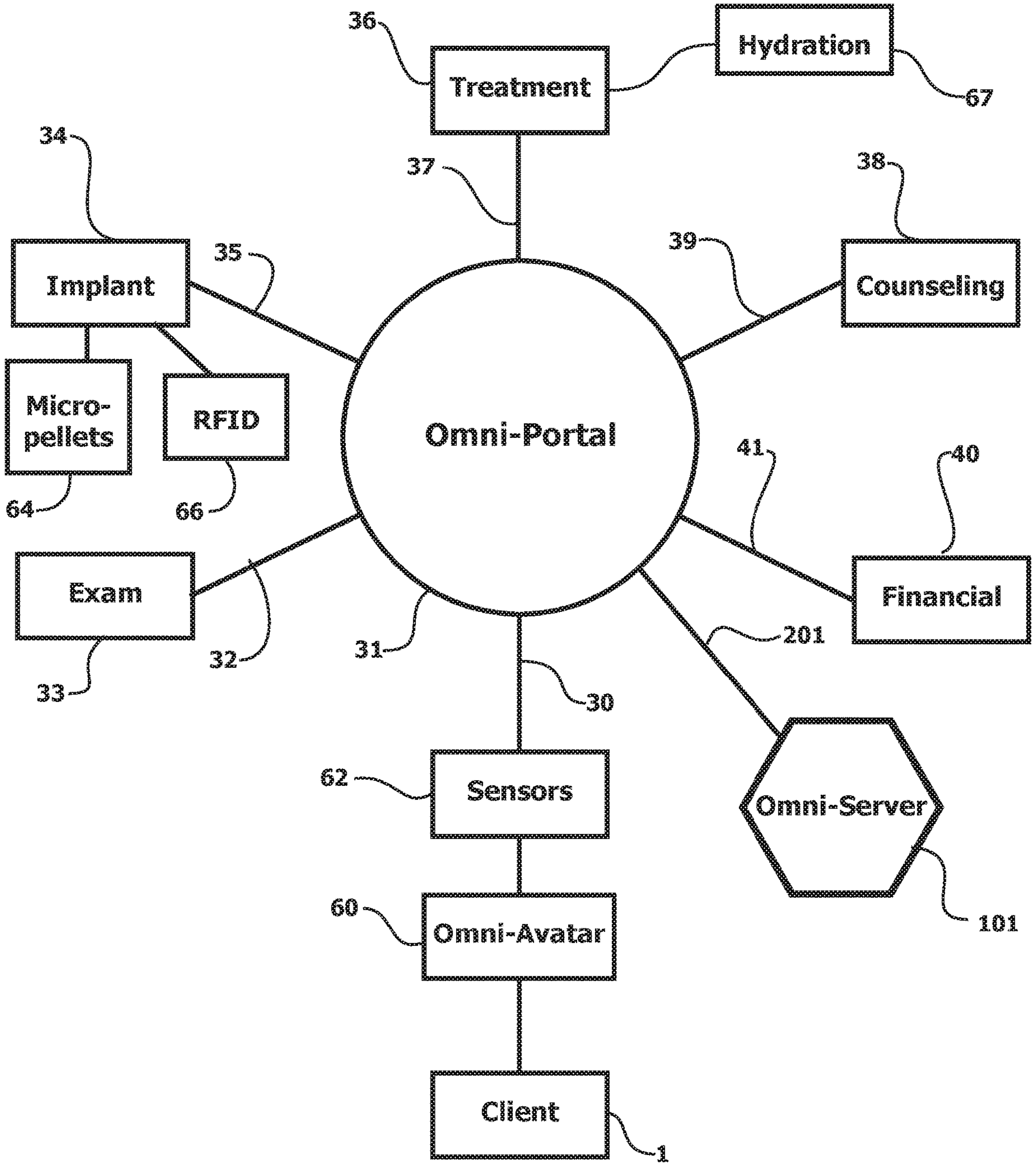
FIG. 5 illustrates a method of the present invention with a portal that is central to all the supporting aspects for a comprehensive recovery program.

FIG. 5 shows an embodiment of the present invention with a Client 1 making a connection 30 with a treatment facility called an Omni-Portal 31. The Omni-Portal 31 may be a free-standing building or a suite of offices that is equipped with one or more Holographical Reality systems that is networked with an Omni-Server 101 to manage the advanced video communication. A staff member or an Omni-Avatar 60 will provide an introduction to the treatment program. An Omni-Avatar 60 is video or a computer generated lifelike image of a staff member that is a life-size, three dimensional embodiment displayed in Holographical Reality on an Omni-Carriage. The Omni-Avatar 60 will respond to sensors 62 that may include motion sensors, proximity sensors, video recognition, voice recognition, and/or other methods of recognizing a person's presence and interaction. The sensors will respond to the actions of the Client 1 to activate the Omni-Avatar 60 to welcome them to the Omni-Portal 31 and proceed to gather basic information for enrollment. The Omni-Avatar 60 may respond with a series of pre-recorded video segments of an actual person or may respond with a live computer generated lifelike image based on the logic of an Artificial Intelligence "AI" program.

Once a staff member or the Omni-Avatar 60 has taken the basic information for enrollment, professionally qualified Doctors and psychiatrists will conduct the Client 1 evaluation over a distance using Holographical Reality. At the Omni-Portal 31 communication 32 may be established for the Client 1 to have an exam 33. At the Omni-Portal 31 a staff member or an automated process will communicate 41 to make financial arrangements 40 for the Client 1 to have treatment. These financial arrangements 40 may be Medicare, Medicaid, insurance, private pay or other payment methods. The medical results of the exam 33 and the financial 40 information will be uploaded to the Omni-Server 101 at a national or international data center for access by the Omni-Portal 31. A treatment program will be scheduled that will be delivered under the process called the Delaney Method.

Following the Exam 33 the staff at the Omni-Portal 31 will communicate 35 with the certified staff to proceed with an implant 34 for the Client 1. The implant 34 may be comprised of "micro-pellets" 64, which is an innovative step that overcomes the problems associated with the present embodiment of larger pellets with medication and their insertion. The micro-pellets 64 are configured preferably smaller than a grain of rice, which therefore do not require a surgical incision with the resulting need for stitches. The micro-pellets 64 are injected beneath the skin without the need for surgery. The site of the injection recovers within one or two days and does not leave a scar. With the administration of a local numbing agent, the Client 1 will not feel pain during the ten minute procedure.

A first implementation may include four micro-pellets 64 that may be 250 mg each. These may be spaced a quarter of an inch or more apart. With this system of proprietary micro-pellets 64, the Client 1 may receive a slow release of the medication over a duration of 90 days.

The system of the present invention provides for the insertion of the micro pellets 64 positioned along "Langer Lines" defined by the integral grain of the skin, which is aligned to allow for stretching in the direction of movement surrounding the body. In this embodiment the selected Langer Lines may be along the horizontal alignment surrounding the hip along the beltline, namely, between and parallel with the Langer Lines. The specific location of insertion may be along this horizontal Langer Line at the back portion of the body. In order to minimize the sensation of awareness of the insertion within individuals, a right handed person may have the insertion in the left portion of the back. Conversely, a left handed person may have the insertion in the right portion of the back.

The micro-pellets 64 may be a proprietary formulation of medication for the addictive or non-addictive treatment. For drug addiction the medication may include stearic acid that will support the effective medical delivery of the opiate antagonist medication over a 90 day period. For autoimmune diseases the medication may be specific to the disease.

Once the implant 34 is complete the Client 1 will receive treatment 36 during the duration of the Delaney Method program. This treatment 36 may be scheduled 37 at an Omni-Portal 31 for the Client 1. One aspect of the treatment may be hydration 67, which is a process of injecting the fluids needed to support successful recovery during the program. At an attending physician's prescription and instruction, immediately after each micro pellet implantation and at a repeated cadence over time, there may be offered to the patient and the patient might agree to receive intravenous hydration 67. Most addicts are woefully dehydrated. For the Micro Pellets to dissolve evenly over time, each patient might need hydration 67.

Also, during the program established in the Delaney Method the Omni-Portal 31 will establish communication 39 for counseling 38 for the Client 1. This may involve having the Client 1 come to the Omni-Portal 31 to meet with a counselor in person or through advanced live video communication.

Figure 6:
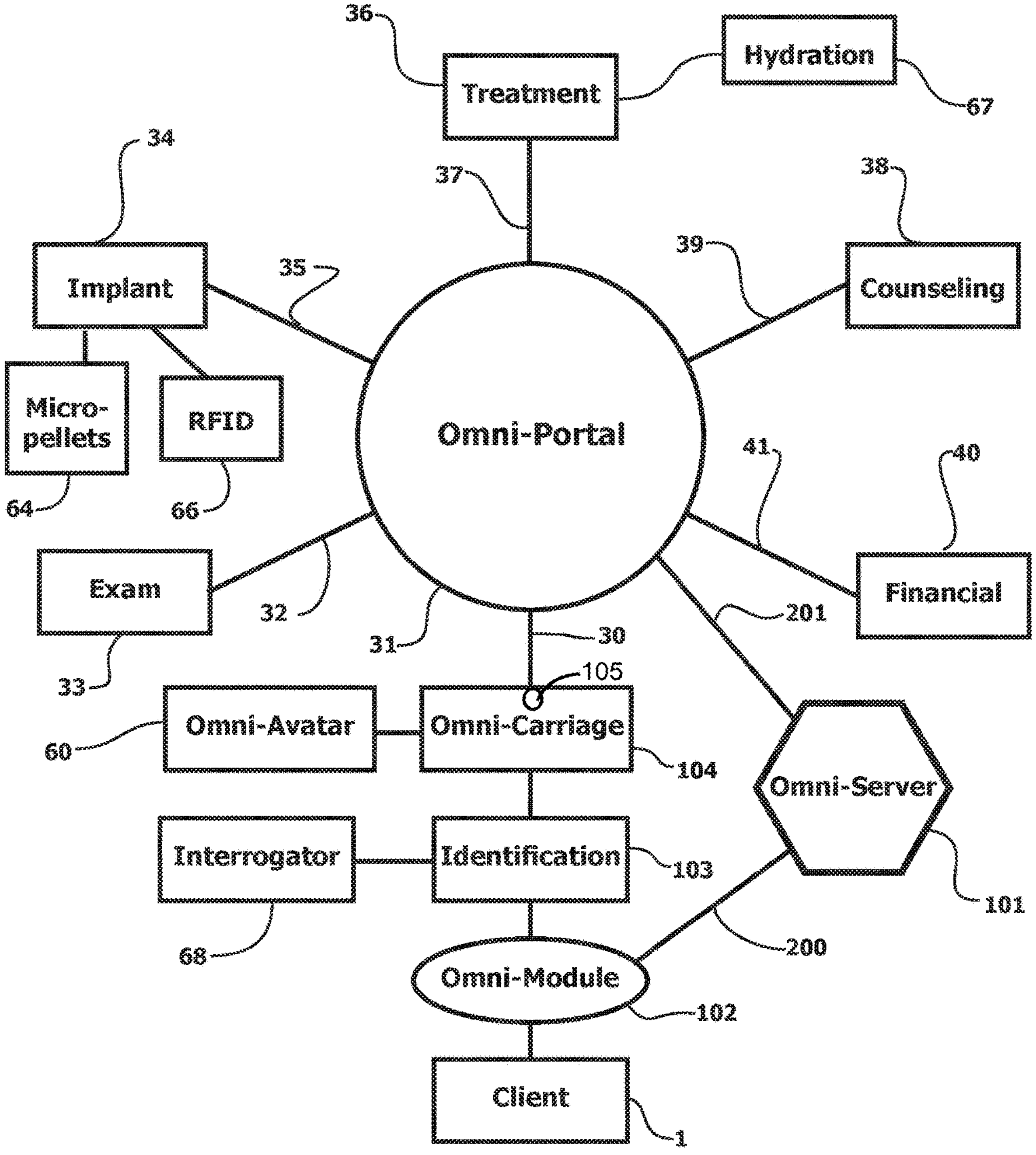
FIG. 6 illustrates an implementation of the method of this present invention that provides a Client with a treatment module through a method of identification to access an advanced video communication system with a networked portal for delivery of generated video content and live video communication for their treatment program.

FIG. 6 shows that a Client 1 may go to an unmanned enclosure holding an advanced video communication system, called an Omni-Module 102, during the duration of the treatment in the Delaney Method. The term "module" can be related to the association with the "lunar module" used for the enclosure for the astronauts during the trip to the moon. In this context, an "Omni-Module" 102 could be the enclosure for an Omni-Carriage 104 where a Client 1 would be transmitted through Holographical Reality to another part of the country or another part of the world. An Omni-Module 102 may be no larger than the size needed for an Omni-Carriage 104 with seating to accommodate a Client for a Holographical Reality experience with a caregiver being transmitted from another location. The size of the footprint of the Omni-Module 102 may be approximately 5' wide and 7' long. The Omni-Module 102 may not have windows or openings that would allow visual access from the outside. Furthermore, the Omni-Module 102 may contain the audio of the communication within the enclosure by the means of construction and acoustic treatment so that the voices of the participants cannot be heard outside. In order to further assure that the voices of the participants are not recognizable from outside of the room a generator of white noise may be used to mask the voices. An Omni-Module 102 will be small enough that it could be set in available spaces in community centers, churches, local government facilities, etc. Furthermore, it could be licensed to be installed within commercial venues, such as Walmart, CVS, Walgreens, etc. With a national network in the United States, Clients could go to any Omni-Module 102 to have their caregiver teleported to meet with them.

An Omni-Module 102 would have an identification method to authorize entry by a Client 1 without any staff at that location. The identification may be by an issued ID card, facial recognition, voice recognition, RFID microchip 66 or other approved identity method. With approval of identity of a Client 1, the door to the Omni-Module 102 would be unlocked and the Omni-Server 101 database would be instantly retrieved for the Client 1. Upon entering the Omni-Module 102 the Holographical Reality visual and audio content would be initiated. One of the advantages of Omni-Modules is that the Clients could gain access to addiction services even in locations where there are not medical staff present or caregivers within hundreds of miles. A further advantage of Omni-Modules is that Clients could seek help without revealing to people in their community that they have addiction problems. In traditional methods of treatment, the addicts need to meet with staff members of the treatment facilities in their own community for care. As a result, many addicts may not seek treatment due to their fear of being recognized during treatment and risk being outcast within their community.

The Client 1 may unlock the door to the Omni-Module 102 using a method of identification 103. The identification 103 will also trigger the Omni-Server 101 of the network of Omni-Portals 31 to begin to deliver advanced video communication to a suite of furniture and audio-visual equipment, called an Omni-Carriage 104. It is through the Omni-Carriage 104 that the services of the Omni-Portal 31 may be delivered through live, prerecorded and computer generated advanced video communication.

An essential aspect of the method of the present invention is the identification of the Client 1. In particular, the system of implanting micro-pellets 64 provides effective delivery of medication over an extended period of time, but the implant is only one part of the comprehensive treatment program. The present method includes a program of medical treatments and counseling by accredited therapists. This requires that the Client 1 has a method for identification with access to the medical records for the treatment program.

Upon admission to a treatment program, a Client 1 may receive an identification card with a method of reading the Client identity, such as a magnetic strip, RFID microchip 66, QR code or other technology for retrieving information. This card may be used upon the return of the Client 1 to a medical treatment location. However, it would be advantageous to have an additional method of identification since the Client 1 may lose the card or forget to bring it to an appointment.

At an initial medical exam, the Client 1 may be able to prove his or her identity.

However, during a treatment period that may have a duration of twelve months, they may not retain the identity card. In the case of an incident needing medical attention, the Client could suffer serious consequences or even death if there is not a way to quickly confirm the contents of their imbedded medication.

Clients with alcohol or drug addiction may not have standard forms of identification, such as a driver's license. They may not have a permanent address. It may be that these Clients do not have medical insurance cards since they may not have any form of insurance. While they may remember their social security number, the confirmation of their identity may be difficult considering their addictive condition. The Client 1 could be given identifying codes or passwords, but these may be forgotten. They may start their treatment at one clinic but over the duration of the treatment program they may move to another city or another state.

Therefore, it is important to be able to prove the identity of the Client through the duration of the treatment program. The preferred method of identification is to avoid a manual process of reviewing paperwork or manually logging into various databases to access information that can be both time consuming and unreliable.

It is thus another objective of this present invention to implement identification methods that are both instantaneous and automated to initiate video communication programs and live video communications that are specific to the Client 1 at the appropriate stage of their treatment program. This Delaney Method may quickly and efficiently identify the Client to receive the treatment services of their program without needing to fill out any paperwork upon arriving at any Omni-Portal 31 or Omni-Module 102.

In another embodiment of the present invention a suite of furniture with integrated audio-visual equipment configured to deliver Holographical Reality communications between the Client and professionals administering the treatment program and furthermore, will facilitate one or more methods for identification. This Omni-Carriage within an Omni-Portal will be networked to the Omni-Server 101 of the national or international database of the Omni-Portals 31. The Omni-Carriage will provide a chair for the Client 1 and table between the Client 1 and the transmitted professional caregiver appearing life-size three dimensionally across the table from the Client while making eye contact during two-way communication in real time. This suite of furniture and equipment is the Omni-Carriage 104.

A camera, as an integral component of the Omni-Carriage 104, will capture an image of the Client 1 seated in a position for a counseling session. A high definition digital photo and/or a video segment may be captured to be stored within the database of the Omni-Portal where it will be saved in the medical records of the Client 1. Upon the initiation of a counseling session, the digital photo or video may be used to identify the Client 1. In a further method of identification, a microphone as an integral component of the Omni-Carriage 104 may capture an audio recording of the Client 1 to be stored at a database of the Omni-Server 101 of Omni-Portal 31 for identification by voice recognition.

Additionally, a facial recognition system may be integrated into the Omni-Carriage 104 for the purpose of providing an accurate identity of the Client 1. In a further method of identification, a significant and yet non-obvious embodiment of this present invention is the insertion of a Radio Frequency Identification Device 66 at the time of the first insertion of the micro-pellets 64. In this system the selected RFID microchip 66 may be smaller than a grain of rice. It would be inserted in a similar method as the micro-pellets 64 and would be inserted at the same time as the procedure for the micro-pellets 64 with medication. This would not require any significant additional time for the procedure and would not impose an additional inconvenience upon the Client 1.

An Omni-Carriage 104 may incorporate a scanning device, called an interrogator 68, to instantly read the code within the RFID microchip 66, which may be linked to a computer within the Omni-Carriage 104 that is networked to the Omni-Portal 31 for identification of the Client 1. The interrogator 68 may be integrated in the back of the chair within the Omni-Carriage 104 to be positioned within 10 cm (4") of the placement of the RFID microchip 66 in the back of the Client 1.

In this embodiment the RFID microchip device 66 would be passive in that it would not have a battery or any internal power source. In this regard, it would be completely inert. The RFID microchip 66 would never wear down and could be good for the lifetime of the Client 1. The specified RFID microchip 66 may be glass encapsulated so that it is biocompatible. This means that it would be non-toxic and would not have any allergic reaction or other adverse effect on the human body.

The RFID microchip device 66 may include a cap made of polypropylene polymer to keep the chip from moving around once it is inserted. The polymer works by encouraging connective tissue and other kinds of cells to form around the capsule to hold it in place. Inside the capsule is a silicon microchip, a tuning capacitor and an antenna coil. In order to retrieve the information on the RFID microchip 66 an interrogator 68 performs the function of energizing the antenna coil to activate the capacitor to read the microchip. When set at the specified frequency the interrogator 68 scans the RFID microchip 66 to receive an identification number.

It is important to note that the RFID microchip 66 only provides an identification number, which does not reveal any personal information about the Client. This ID number is only meaningful when used as identification within an external database. In this regard the application of an RFID microchip 66 meets all HIPAA privacy requirements for confidential medical information or any other privacy requirements. Furthermore, the RFID microchip device 66 can be simply removed by a small incision at any time during the treatment or following the completion of the treatment program.

The comprehensive treatment system of this present invention based on an implanted RFID microchip 66 establishes a platform for the delivery of an extensive host of innovations in the care for Clients needing addiction recovery treatment that has not been possible with previous systems. The simple ID number establishes a link to a database accessed over the Internet for the full scope of innovative services.

While it is important to confirm identity, it is essential that the Client's medical records are confidential. The identification method of this present method using an RFID microchip 66 solves the problems presented above. The RFID microchip 66 does not contain any confidential information since it only retains a single identification number. Furthermore, the RFID microchip 66 is not physically visible when inserted and can be removed at any time during or after the treatment program.

One of the unique benefits of the method using an RFID microchip 66 is that a Client 1 could undergo a treatment program without ever revealing any of their personal information. This may be of extreme importance for individuals who need addiction recovery treatment, but do not want their condition to be known to their employers, insurance providers or other people. These anonymous individuals could undergo their exam for confirmation of their medical condition and pay for their treatment in cash. They could receive the insertion of the micro-pellets 64 and RFID microchip 66 for the treatment. For the duration of the program they would only need to provide access to the code on their RFID microchip 66 to continue with all aspects of treatment.

Another aspect of the present invention is that the method of using visual recognition, voice recognition or an RFID microchip 66 for identification would eliminate the liability of fraud during treatment. The Client 1 could not sell the treatment services to another individual or claim treatment that was not delivered since their identity is confirmed. It may be of particular value to government funded programs where confirmation of services can be validated for recipients.

Further advantages of the above described methods of identity verification may be evident during the treatment period. As the Clients 1 proceed with the program of medical procedures and counseling, the identity will need to be verified multiple times. If the Client 1 is in a poor cognitive state during drug or alcohol recovery their ability to communicate effectively may be compromised. Also, the Client 1 may be of a different nationality and may not have command of the English language to establish their identity.

Once the Client is identified at an Omni-Carriage 104, the Omni-Server 101 is triggered to initiate the current program for the Client 1. This may be a pre-programmed video content that will appear in the Omni-Carriage 104 as a Holographical Reality display. This content may be a video image of person welcoming the Client 1 upon their return for treatment. The selection of the video content may be determined by a sophisticated Artificial Intelligence (AI) program (caregiver 60) that will present a communication response that is uniquely appropriate for the Client 1. The AI response may be a selected pre-recorded video of a caregiver welcoming the Client back. Alternatively, the video may be a real time, computer generated Omni-Avatar 60 appearing life-size in a highly realistic human embodiment. In this modality, the same Omni-Avatar 60 that previously greeted and met with the Client 1 will reappear essentially providing comfort (through continuity) that the same doctor is bedside or in the room with the Client 1.

The Omni-Carriage 104 includes a high definition camera 105 to capture a video image that is transmitted to be viewed by the caregiver for live two-way communication. This same video image may be analyzed by a computer for AI evaluation of facial recognition that may provide information about the emotional state of the Client. The combination of the information in the medical records within the Omni-Portal 31 on the Client 1 and their AI evaluation of their condition will determine the assignment of the appropriate caregiver to be teleported to the Omni-Carriage 104.

Figure 7:
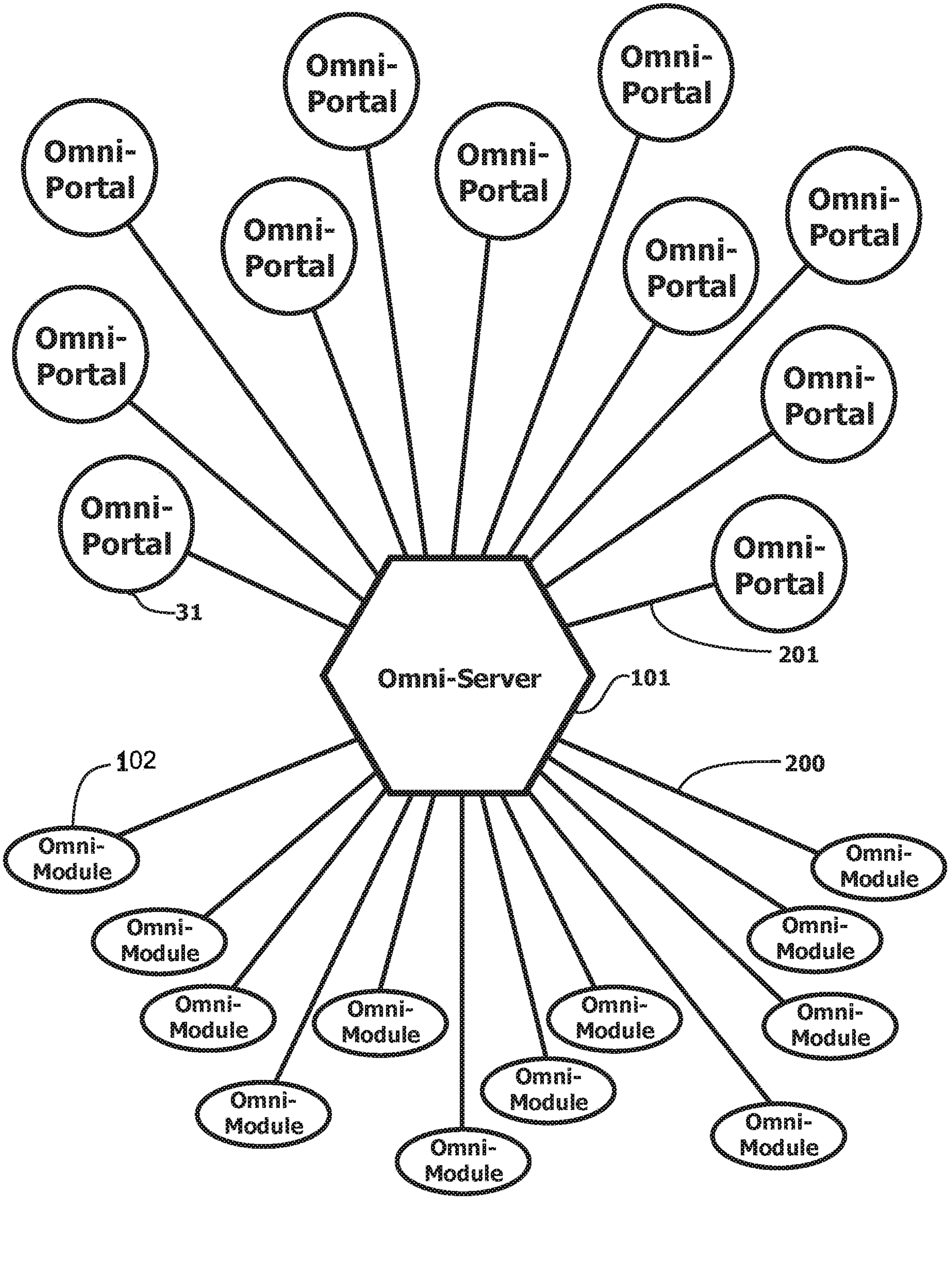
FIG. 7 illustrates an implementation of the present invention that may include a large number of locations for Clients to connect through a server with a large resource of healthcare services

In FIG. 7 Clients may enter an Omni-Module gain access over a network 200 to an Omni-Server 101 that would have their records and progress for their recovery program of the Delany Method. This Omni-Server 101 may initiate communication with service providers at Omni-Portals 201. By virtue of the present invention, there can be a network of thousands of Omni-Portals 31 with communications capabilities for Clients to access caregivers. In cases where the Clients have scheduled follow-up meetings, the Client will go to the nearest Omni-Module 102 for the scheduled session with the assigned caregiver for their treatment. There would not be a need to return to the location at the beginning of the treatment, since each Omni-Module 102 at any location would access the same Omni-Server 101 database with the resource of caregivers for live video communication. In this way services can be delivered without the limitations of geographic proximity. If there is a need for the Client to make contact to a caregiver for an unscheduled time, the next available caregiver will be routed to the Omni-Module 102 for meeting with the Client.

Figure 8:
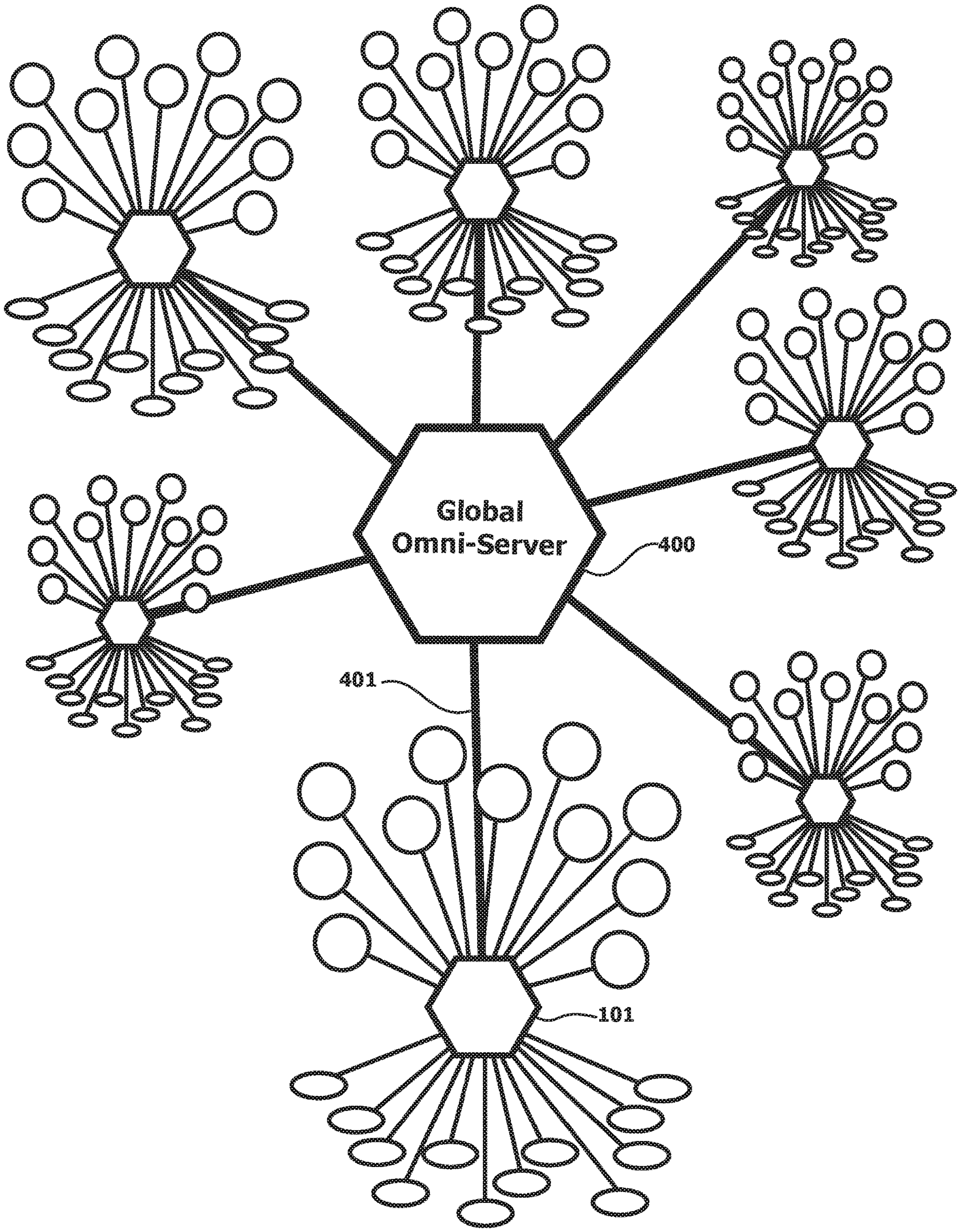
FIG. 8 illustrates an implementation of the present invention with a number of large networked to service organizations managed through a global server.

In FIG. 8 a Global Omni-Server 400 may be connected over a high speed network 401 to Omni-Servers 101 supporting large or national implementations of the Delany Method.

Figure 9:
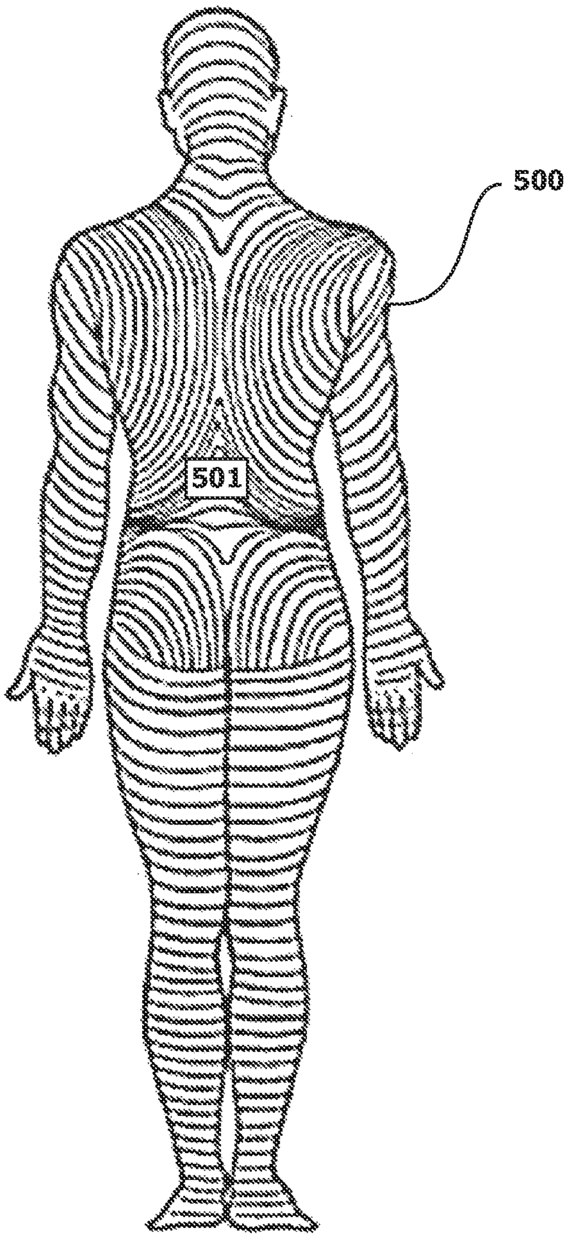
FIG. 9 is a depiction of Langer lines in a human.
Figure 10:
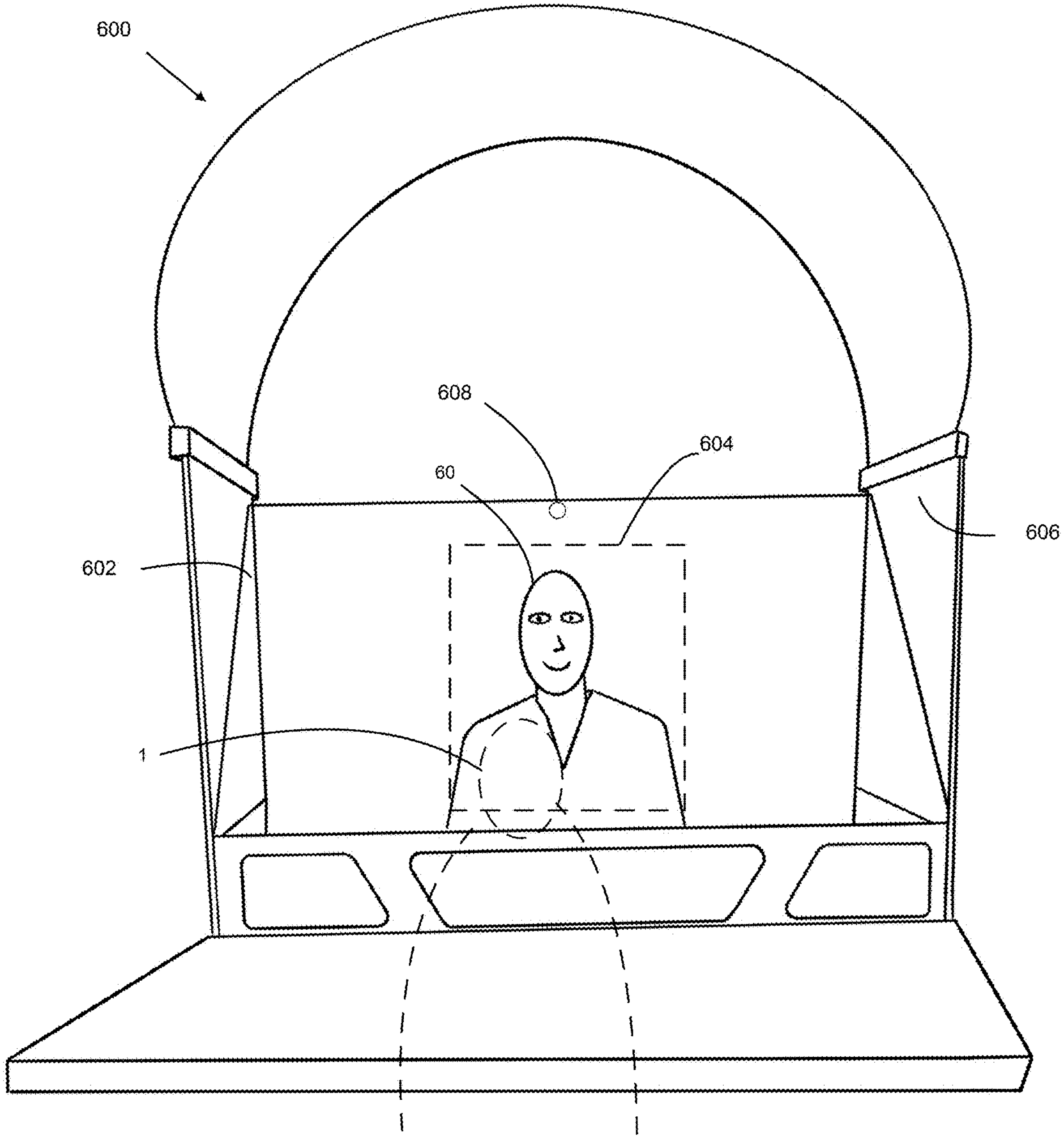
FIG. 10 depicts a video conference system incorporates a two-way mirror between the patient and an image display device.

FIG. 9 shows an illustration of the back of a human body with lines illustrating the Langer Lines 500 defined by the integral gain of the skin. The micro-pellets of the present invention are inserted in a horizontal orientation in the selected Langer Lines 501 along the horizontal alignment surrounding the hip along the beltline.

A video conference system 600 which incorporates a two-way mirror 602 between the Client and an image display device 604 positioned for providing the Client with a direct view looking forward at eye level through the two-way mirror 602 at a displayed image on the image display device 604 while the two-way mirror 602 is angled at approximately 45 degree to reflect an illuminated panel 606 that is positioned further from the two-way mirror 602 than the image display device 604 and a caregiver at a distant location from the Client is captured by a camera 608 with a display system that achieves a line of sight directly toward the camera and the video image and audio is transmitted over an Internet connection to the location of the Client for appearing on the image display device 604 with a perceived eye contact.

What is claimed is:

1. A medical treatment method, which includes:

making ¼ inch long dashed cuts subcutaneously into selected Langer lines of a patient's back with ½ inch spaces between the dashed cuts;

implanting into a patient a micro-pellet into each dashed cut which has medication therein which releases over time, and a video conference system which incorporates a two-way mirror between the patient and an image display device positioned for providing the patient with a direct view looking forward at eye level through the two-way mirror at a displayed image on the image display while the two way mirror is angled at approximately 45 degrees to reflect an illuminated panel that is positioned further from the two-way mirror than the image display device, wherein stored digital files of a recorded video of a caregiver or a live computer generated image of an avatar is transmitted to appear on the image display device for viewing by the patient.

2. A medical treatment method of claim 1, which includes employing an identification device into the patient wherein identification is enabled over the Internet to a secure database associated with medical record and treatment plan data for the identification device of the patient.

3. A medical treatment method of claim 2, wherein the method of identification is an RFID microchip, and an interrogator for reading the RFID microchip and which is positioned at an access point to a video conference system that has an internet connection to the database with the patient's medical records and treatment plan data.

4. A medical treatment method of claim 3, wherein the interrogator is positioned in a back of a chair in which the patient sits.

5. A medical treatment method of claim 1, wherein the micro-pellets are implanted in a horizontal orientation parallel to Langer lines in the horizontal plane surrounding upper hips and lower back.

6. A medical treatment method of claim 1, wherein the micro-pellets are smaller than 1 m in length.

7. A medical treatment method of claim 1, wherein the micro-pellets include Naltrexone.

8. A medical treatment method of claim 7, wherein the micro-pellets include stearic acid.

9. A medical treatment method of claim 1, wherein the micro-pellets remain in the patient for at least three months.

10. A medical treatment method of claim 1, wherein a caregiver at a distant location from the patient is captured by a camera with a display system that achieves a line of sight directly toward the camera and the video image and audio is transmitted over an Internet connection to the location of the patient for appearing on the image display with a perceived eye contact.

11. A medical treatment method, which includes:

making ¼ inch long dashed cuts subcutaneously into in selected Langer lines of a patient's back with ½ inch spaces between the dashed cuts; and implanting into a patient a micro-pellet into each dashed cut which has medication therein which releases over time, and a video conference system which incorporates a two-way mirror between the patient and an image display device positioned for providing the patient with a direct view looking forward at eye level through the two-way mirror at a displayed image on the image display while the two way mirror is angled at approximately 45 degrees to reflect an illuminated panel that is positioned further from the two-way mirror than the image display device, wherein the camera captures a digital image, video file or facial recognition documentation of the patient to be stored in medical records of the patient for identification for approval for usage of the video conference system for the duration of a treatment plan.

12. A medical treatment method of claim 11, wherein a camera is positioned to view the patient as a reflection of the two-way mirror along a line at eye level of the displayed image of a transmitted person appearing on the image display device.

13. A medical treatment method of claim 11, wherein the camera captures a live video image of the patient that is analyzed by a facial recognition application that identifies facial expressions to determine the mental state of the patient.

14. A medical treatment method of claim 11, wherein the method further includes use of an RFID microchip implanted in the patient, and an interrogator for reading the RFID microchip and which is positioned at an access point to a video conference system that has an internet connection to the database with the patient's medical records and treatment plan data.

15. A medical treatment method of claim 14, wherein the interrogator is positioned in a back of a chair in which the patient sits.

16. A medical treatment method of claim 11, wherein the micro-pellets are implanted in a horizontal orientation parallel to Langer lines in the horizontal plane surrounding upper hips and lower back.

17. A medical treatment method of claim 11, wherein the micro-pellets include Naltrexone.

18. A medical treatment method of claim 17, wherein the micro-pellets include stearic acid.

19. A medical treatment method of claim 11, wherein the micro-pellets remain in the patient for at least three months.

20. A medical treatment method, which includes:

making ¼ inch long dashed cuts subcutaneously into in selected Langer lines of a patient's back with ½ inch spaces between the dashed cuts; and implanting into a patient a micro-pellet into each dashed cut which has medication therein which releases over time, and a video conference system which incorporates a two-way mirror between the patient and an image display device positioned for providing the patient with a direct view looking forward at eye level through the two-way mirror at a displayed image on the image display while the two way mirror is angled at approximately 45 degrees to reflect an illuminated panel that is positioned further from the two-way mirror than the image display device, wherein a microphone captures an audio recording of the patient to be stored in medical records of the patient for identification for approval for usage of the video conference system for the duration of a treatment plan.

* * * * *